United States Patent
Alexandre et al.

(10) Patent No.: US 7,981,075 B2
(45) Date of Patent: Jul. 19, 2011

(54) DEVICE FOR NEEDLELESS INJECTION OPERATING WITH TWO CONCENTRIC ENERGETIC MATERIALS

(75) Inventors: Patrick Alexandre, Gray (FR); Bernard Brouquieres, Toulon (FR); Philippe Gautier, Le Plessis Pate (FR); Christiane Reynaud, Mennecy (FR)

(73) Assignee: Crossject, Paris (FR)

( * ) Notice: Subject to any disclaimer, the term of this patent is extended or adjusted under 35 U.S.C. 154(b) by 660 days.

(21) Appl. No.: 11/662,226

(22) PCT Filed: Sep. 20, 2005

(86) PCT No.: PCT/FR2005/002325
§ 371 (c)(1),
(2), (4) Date: Mar. 8, 2007

(87) PCT Pub. No.: WO2006/032775
PCT Pub. Date: Mar. 30, 2006

(65) Prior Publication Data
US 2007/0276321 A1 Nov. 29, 2007

(30) Foreign Application Priority Data
Sep. 21, 2004 (FR) ...................................... 04 09951

(51) Int. Cl.
*A61M 5/30* (2006.01)
(52) U.S. Cl. .......................................................... 604/69
(58) Field of Classification Search ..................... 604/69, 604/68, 70, 141, 143, 146, 147, 140
See application file for complete search history.

(56) References Cited

U.S. PATENT DOCUMENTS

| 2,322,244 A | 6/1943 | Lockhart | |
|---|---|---|---|
| 2,704,542 A | 3/1955 | Scherer | |
| 4,000,022 A * | 12/1976 | Beckert et al. | 149/19.3 |
| 4,519,855 A * | 5/1985 | Leneveu et al. | 149/21 |
| 5,672,842 A * | 9/1997 | Brion et al. | 102/282 |
| 6,322,649 B1 * | 11/2001 | Marsaud et al. | 149/10 |
| 6,843,868 B1 * | 1/2005 | Fawls et al. | 149/19.3 |
| 2002/0007885 A1 * | 1/2002 | Serizawa et al. | 149/46 |
| 2002/0161329 A1 | 10/2002 | Gonnelli et al. | |
| 2003/0135155 A1 | 7/2003 | Alexandre et al. | |

FOREIGN PATENT DOCUMENTS

| EP | 0 585 612 A2 | 3/1994 |
|---|---|---|
| FR | 2 807 946 | 10/2001 |
| GB | 835560 | 5/1960 |
| WO | WO 98/31409 | 7/1998 |

\* cited by examiner

*Primary Examiner* — Nicholas D Lucchesi
*Assistant Examiner* — Brooke M Matney
(74) *Attorney, Agent, or Firm* — Oliff & Berridge, PLC

(57) ABSTRACT

A needleless injection device used for intradermal, subcutaneous and intramuscular injections is disclosed. The device includes a pyrotechnic gas generator, at least one piston, a reserve of liquid active principle and an injection nozzle. The generator includes a pyrotechnic charge composed of a central energetic material that is surrounded by a second peripheral energetic material. The entire outer surface of the central energetic material contacts the inner surface of the peripheral energetic material. The two energetic materials have different rates of combustion.

20 Claims, 2 Drawing Sheets

DEVICE FOR NEEDLELESS INJECTION OPERATING WITH TWO CONCENTRIC ENERGETIC MATERIALS

The technical field of the invention is that of prefilled and disposable needleless syringes functioning with a gas generator and used for intradermal, subcutaneous and intramuscular injections of liquid active principle for therapeutic use in human or veterinary medicine.

For the injection devices according to the invention, a liquid active principle is composed of a more or less viscous liquid, or a liquid mixture, or a gel. The active principle can be a solid dissolved in a suitable solvent for injection. It can also be represented by a powdered solid in more or less concentrated suspension in a suitable liquid. The particle size of the principle must be compatible with the diameter of the conduits in order to avoid blockages.

The use of a pyrotechnic charge for this type of syringe is already known and has been the subject of several patents. By way of example, mention may be made of the U.S. Pat. No. 2,322,244 relating to a needleless hypodermic injector functioning on the basis of a blank cartridge. The liquid to be injected, being placed in contact with the cartridge, is expelled from the injector under the effect of the pressure generated by the combustion gases. Another patent, WO 98/31409, describes a hypodermic injection system involving a pyrotechnic charge composed of an explosive or of a powder. The specific feature of this injector is that it is designed to regulate the problems associated with the kinetics of expulsion of the liquid active principle, not by acting on the characteristics of the pyrotechnic composition, but by presenting a special geometry that defines in particular an adjacent gas expansion chamber equipped with a vent. The pyrotechnic charge, situated in immediate proximity to the liquid active principle, acts directly and instantaneously on said principle by giving it a very high initial speed, while the gases invade the main chamber and the adjacent chamber. The pressure exerted on the active principle then decreases and fixes at an almost constant value sufficient to cause said active principle to penetrate the patient's skin. The adjacent chamber makes it possible to regulate this pressure. The U.S. Pat. No. 2,704,542 relates to a method of injection by a jet of liquid. This method does not specifically entail a pyrotechnic charge, but involves a device intended to control the pressure profiles. The method used to achieve this objective lies in the sliding movement of a two-part piston made up of a central cylinder of small cross section housed in a hollow cylinder. An upstream pressure first provokes a displacement of small amplitude of the central cylinder so as to impart a brief but very intense impulse to the liquid to be expelled, then the whole piston is displaced so as to continue to expel said liquid, at the appropriate pressure, in order to ensure good penetration.

In order to control the pressure profiles without having to modify the geometric characteristics of the injector, it has been proposed, in patent FR 2 807 946, to design a needleless injector equipped with a gas generator involving a pyrotechnic charge composed of the mixture of a slow-burning powder with a fast-burning powder. The fast-burning powder ensures an abrupt rise in pressure in order to give the active principle a speed sufficient to penetrate the skin, and the slow-burning powder being chosen to guarantee a depth of injection once the skin has been punctured. United States patent application US 2002/0161329 also mentions the use of two powders in an injection device, said powders having different combustion characteristics.

By contrast, in the prior art, there are no needleless injectors involving a pyrotechnic charge composed of the combination of a central energetic material and a peripheral energetic material with different rates of combustion. By this means, the pyrotechnic charge, which can be monolithic or divided into several grains, maintains substantial homogeneity regarding the geometric distribution of the two types of energetic material, thus giving the injection devices according to the invention a character of great reliability and reproducibility in the control of the pressure profiles. This particular geometry of the pyrotechnic charge results from simple production methods which are already well-proven and are very well controlled.

In the remainder of the description, the term "energetic material" covers all pyrotechnic substances able to burn, whether gun powder or pellet powder, propergol, or even explosives.

The subject of the present invention is a needleless injection device comprising a pyrotechnic gas generator, at least one piston, a reserve of liquid active principle, and an injection nozzle, characterized in that said generator comprises a pyrotechnic charge composed of a central energetic material surrounded by a second, peripheral energetic material, the two energetic materials having different rates of combustion.

Preferably, the gas generator comprises an ignition system for initiating the combustion of the peripheral energetic material, in such a way that the combustion front develops from the periphery of the pyrotechnic charge to its centre.

With a pyrotechnic charge of this kind and an ignition system of this kind, and depending on the compositions chosen for the two energetic materials, it is possible to envision a multiplicity of pressure profiles as a function of time at the outlet of the injection nozzle.

According to a first preferred embodiment of the invention, the peripheral energetic material is selected from among compositions which burn very slowly, such that it produces a greater or lesser pyrotechnic delay for the combustion of the central energetic material.

According to a second preferred embodiment of the invention, the peripheral energetic material is selected from among compositions which burn very quickly, such that the combustion of said material produces instantaneously a pressure peak of high intensity promoting perforation of the skin.

The ignition systems used for the injection devices according to the invention have customary and well-proven characteristics and may entail, for example, either a hot wire through which an electric current runs, or a primer that can be initiated electrically or by percussion.

The two energetic materials having different combustion characteristics, the principle of this type of pyrotechnic charge is to induce a twin combustion regime resulting in at least two distinct phases in the pressure variation at the injection nozzle outlet, making it possible to solve the twin problem of penetration of the active principle through the skin and control of the depth of injection once the skin has been punctured.

Advantageously, the peripheral energetic material is in the solid state, such that it constitutes an envelope for the central energetic material.

The two energetic materials are preferably in contact with one another, such that the combustion front is transmitted from one energetic material to the other.

Advantageously, the entire outer surface of the central energetic material is in contact with the inner surface of the peripheral energetic material.

According to a first preferred embodiment of the invention, the pyrotechnic charge is a powder made up of several grains, each grain being composed of a central energetic material surrounded by a peripheral energetic material, the two energetic materials having different rates of combustion.

Advantageously, the gas generator comprises a single pyrotechnic charge made up of a powder, and the peripheral energetic material has a rate of combustion greater than that of the central energetic material. In this way, at the start of combustion, the pressure increases rapidly to reach a threshold value, then, once the central energetic material begins to burn, the pressure decreases before stabilizing at a predetermined level below the aforementioned threshold value. The initial pressure threshold allows the active principle to puncture the skin of the patient to be treated, while the pressure obtained in the following phase allows the active principle to penetrate the patient's skin to a given depth. Conversely, it is possible to choose a peripheral energetic material having a rate of combustion lower than that of the central energetic material so as to introduce a pyrotechnic delay with respect to the combustion of the central energetic material.

According to a second preferred embodiment of the invention, the gas generator is formed by a mixture of two powders each having several grains, one being composed of a single energetic material, and the other being composed of a central energetic material surrounded by a peripheral energetic material having different rates of combustion.

Advantageously, the powder composed of two different energetic materials is obtained from a smoothing operation. The smoothing consists in penetration, by diffusion, of a chemical agent which modifies the composition of the energetic material, hence its energy level and its rate of combustion.

According to a preferred embodiment of the invention, said powder is obtained from a coating operation. The coating consists in depositing, around the grain of energetic material, a film of known thickness of an energetic or inert material with controlled combustion characteristics, for example the rate of combustion.

According to a third preferred embodiment of the invention, the pyrotechnic charge is composed of a monolithic block. Said block can, for example, be cylindrical and have a central channel in the manner of the geometry of the blocks of propergol produced in mass propulsion.

According to another preferred variant of the invention, the central energetic material is in the liquid state and the peripheral energetic material is in the solid state. The liquid energetic material can, for example, be an ergol.

According to a preferred embodiment of the invention, the central energetic material is in the gel state and the peripheral energetic material is in the solid state. The energetic material in the gel state can, for example, also be an ergol.

Advantageously, the pyrotechnic charge composed of a central energetic material in the liquid state or gel state and of a peripheral energetic material in the solid state is obtained by a process of encapsulation.

The encapsulation consists in generating a shell of energetic or inert product enclosing solid, liquid or gel-like materials.

According to a preferred embodiment of the invention, the central energetic material is composed of a powder made up of at least one grain, and the peripheral energetic material is composed of a nitrofilm.

Advantageously, the nitrofilm comprises a plasticizer, a stabilizer and nitrocellulose.

Preferably, the powder is a homogeneous powder based on nitrocellulose.

Advantageously, the powder contains nitroglycerine.

The nitrofilm preferably constitutes a closed envelope for the grains of powder.

The nitrofilm serves, on the one hand, as a receptacle for the powder in order to facilitate its integration in the generator and, on the other hand, it promotes the ignition of the powder by virtue of its capacity to be easily initiated in combustion and by virtue of its high rate of combustion.

The needleless injection devices according to the invention have the advantage of guaranteeing satisfactory injection of the entirety of the liquid active principle, using a simple operating mechanism and taking up a small space, requiring neither specific parts, machining or additional costs, nor modification of the geometry of the body of said syringes.

Moreover, the wide variability of the compositions that can be used for the pyrotechnic charges included in the injection devices according to the invention means that it is possible to achieve a very wide variety of pressure profiles which may be adapted to all possible configurations. Finally, the perfect control of the effects generated by the combustion of a pyrotechnic charge combined with widely proven ignition systems means that the needleless syringes according to the invention are very reliable and safe.

Figure 1:
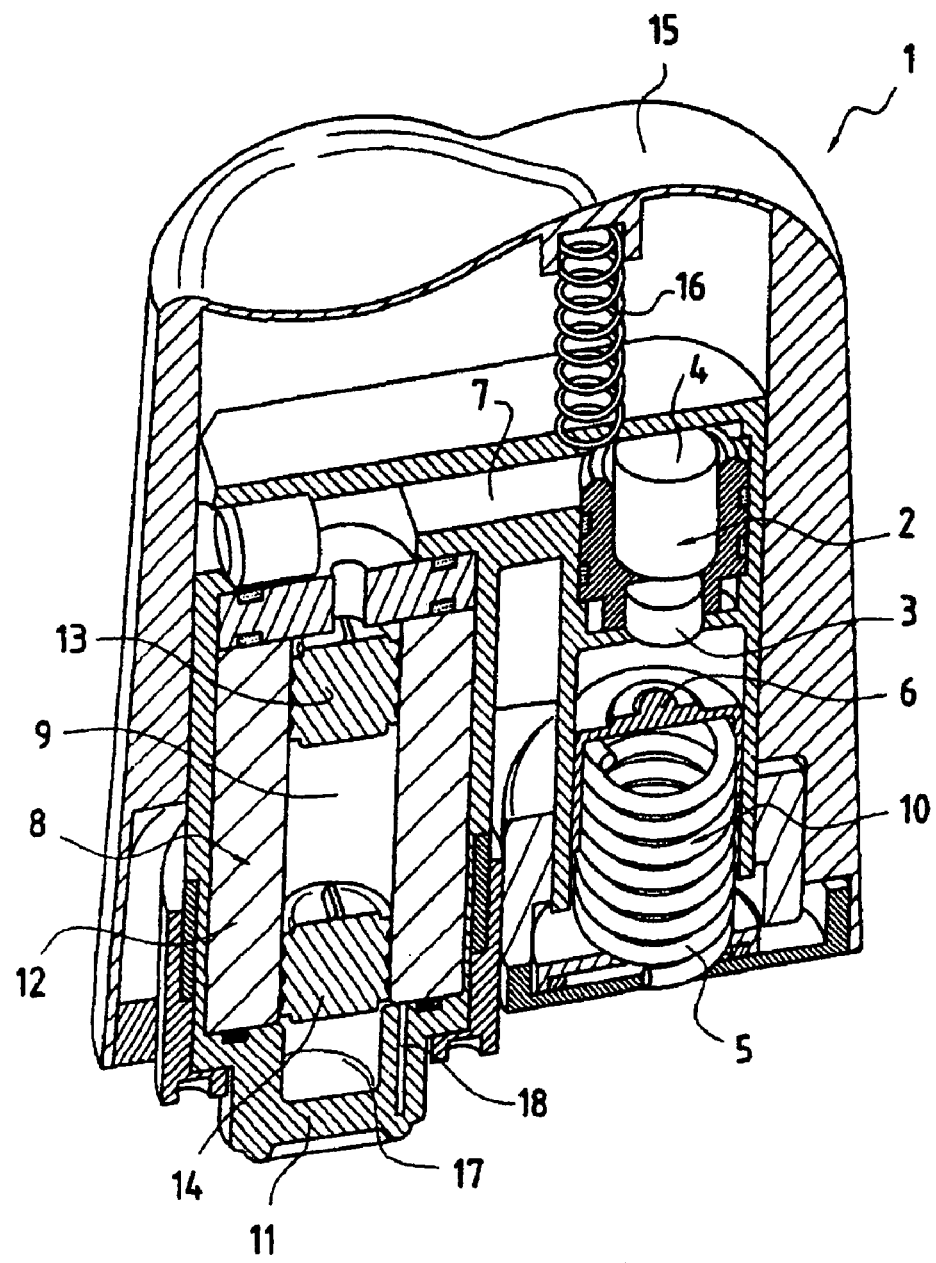
FIG. 1 is a longitudinal axial section through a needleless injection device according to the invention.

Referring to FIG. 1, a needleless injector 1 according to the invention comprises a pyrotechnic gas generator 2 made up of a primer 3 and a pyrotechnic charge 4, an ignition system 10 comprising a pretensioned spring 5 and a striker 6, a combustion chamber 7, a liquid column 8 including the liquid active principle 9 to be injected, and an injection nozzle 11. The column of liquid 9 comprises a glass tube 12 closed by two stopper plugs 13, 14 between which is situated said liquid active principle 9 to be injected. The injector 1 according to the invention is provided with a trigger system formed by a hood 15 and a spring 16 which is able to compress under the effect of the displacement of said hood 15.

The mode of functioning of a needleless injector 1 according to the invention is the following.

The injector is positioned in such a way that the nozzle 11 bears against the skin of the patient to be treated.

A pressure exerted on the hood 15 causes the displacement of said hood 15 which is made resistant by the effect of the spring 16 which compresses. Beyond a threshold depression of said hood 15, the ignition system 10 is released, resulting in the relaxation of the pretensioned spring 5 and, therefore, the abrupt displacement of the striker 6 which is joined to it. Said striker 6 impacts the primer 3 which is set in combustion, inducing the combustion of the pyrotechnic charge 4. The gases emitted by the combustion of said charge 4 pressurize the combustion chamber 7, thus provoking displacement of the liquid column 8. The downstream piston plug 14, which is situated nearest to the nozzle 11, comes to lie in a space 17 provided for this purpose, while the upstream piston plug 13 which is situated nearest to the combustion chamber 7 continues to move, exerting a pressure on the liquid 9 to be injected. Said liquid 9 then escapes via an injection channel 18 situated in the nozzle 11 and freed by the downstream piston plug 14. The injection continues until the upstream piston plug 13 comes into contact with the downstream piston plug 14.

The following non-limiting examples illustrate the main characteristic of the invention concerning the pyrotechnic charge 4.

EXAMPLE 1

Figure 2:
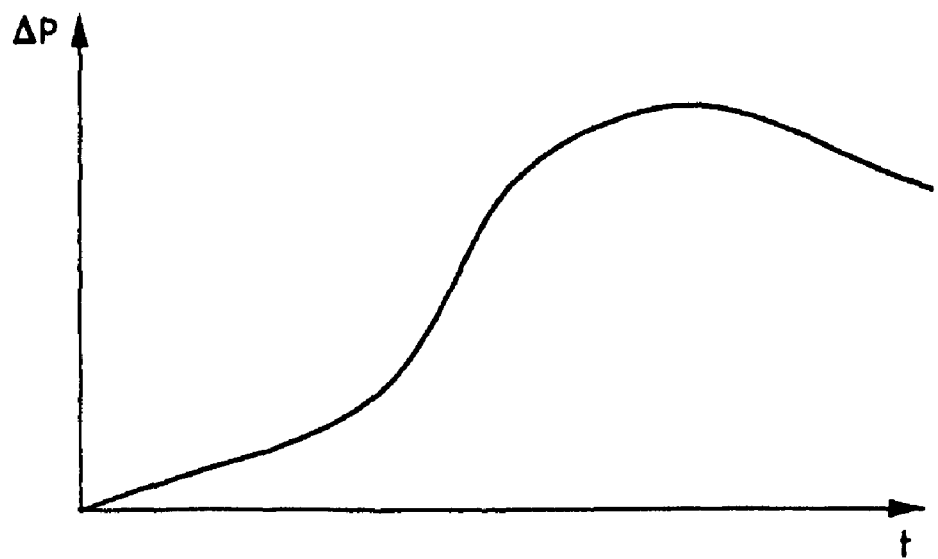
FIG. 2 is a simplified graph representative of the pressure variation at the nozzle outlet over time, generated by the combustion of a single powder in which the peripheral energetic material has a rate of combustion less than that of the central energetic material.

The pyrotechnic charge is composed of a single powder, and the peripheral energetic material has a rate of combustion less than that of the central energetic material. A representative pressure profile obtained as a function of time at the nozzle is shown in FIG. 2. In a first phase, the combustion of the peripheral energetic material leads to a slight increase in the pressure. In a second phase, the pressure increases abruptly due to the combustion of the central energetic material. Finally, the pressure slowly decreases.

EXAMPLE 2

Figure 3:
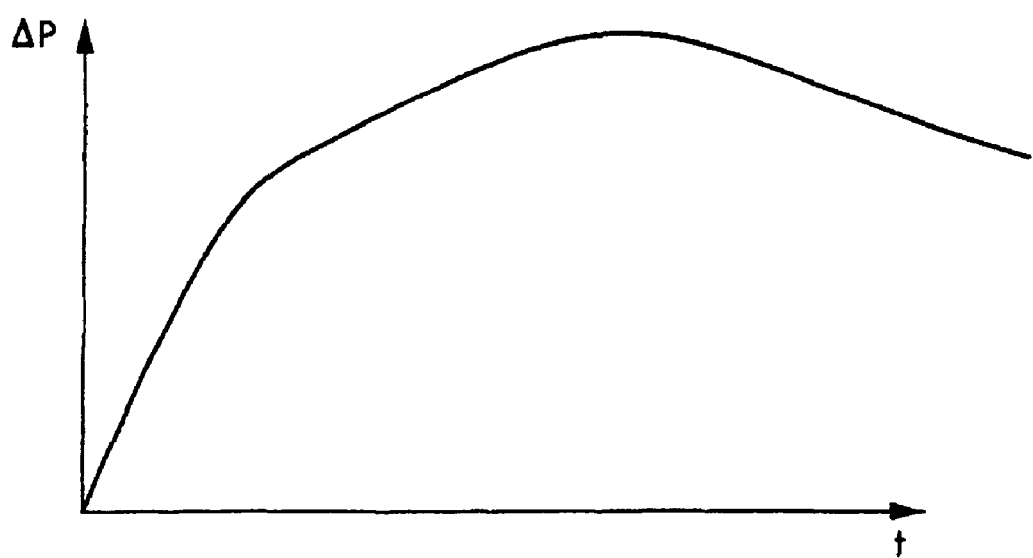
FIG. 3 is a simplified graph representative of the pressure variation at the nozzle outlet over time, generated by the combustion of a single powder in which the peripheral energetic material has a rate of combustion greater than that of the central energetic material.

The pyrotechnic charge is composed of a single powder, and the peripheral energetic material has a rate of combustion greater than that of the central energetic material. A representative pressure profile obtained as a function of time at the nozzle is shown in FIG. 3. In a first phase, the pressure increases abruptly due to the combustion of the peripheral energetic material. In a second phase, the pressure continues to increase more gradually, and, finally, said pressure slowly decreases.

The large numbers of existing pyrotechnic compositions that can be used in the needleless injection devices according to the invention permit a wide variation in the pressure profiles at the nozzle outlet, thus making it possible to treat a large number of configurations.

The invention claimed is:

1. Needleless injection device comprising a pyrotechnic gas generator including a pyrotechnic charge composed of two energetic materials having different rates of combustion, at least one piston, a reserve of liquid active principle, and an injection nozzle, wherein one of the two energetic materials is central and is surrounded by the other energetic material which is peripheral, and the whole of the outer surface of the central energetic material is in contact with the inner surface of the peripheral energetic material.

2. Device according to claim 1, wherein the peripheral energetic material is in the solid state.

3. Device according to claim 2, wherein the two energetic materials are in contact with one another.

4. Device according to claim 2, wherein the central energetic material is in the liquid state.

5. Device according to claim 4, wherein the pyrotechnic charge is obtained by a process of encapsulation.

6. Device according to claim 2, wherein the central energetic material is in the gel state.

7. Device according to claim 6, wherein the pyrotechnic charge is obtained by a process of encapsulation.

8. Device according to claim 1, wherein the pyrotechnic charge is a powder made up of several grains, each grain being composed of a central energetic material surrounded by a peripheral energetic material, the two energetic materials having different rates of combustion.

9. Device according to claim 8, wherein the gas generator comprises a single pyrotechnic charge formed from a powder, and the peripheral energetic material has a rate of combustion greater than that of the central energetic material.

10. Device according to claim 8, wherein the powder is obtained from a smoothing operation.

11. Device according to claim 8, wherein the powder is obtained from a coating operation.

12. Device according to claim 1, wherein the gas generator is formed by a mixture of two powders, each having several grains, one being composed of a single energetic material and the other being composed of a central energetic material surrounded by a peripheral energetic material having different rates of combustion.

13. Device according to claim 1, wherein the pyrotechnic charge is composed of a monolithic block.

14. Device according to claim 1, wherein the central energetic material is composed of at least one powder made up of at least one grain, and the peripheral energetic material is composed of a nitrofilm.

15. Device according to claim 14, wherein the nitrofilm comprises a plasticizer, a stabilizer and nitrocellulose.

16. Device according to claim 14, wherein the powder is a homogeneous powder based on nitrocellulose.

17. Device according to claim 16, wherein the powder contains nitroglycerine.

18. Device according to claim 14, wherein the nitrofilm constitutes a closed envelope for the powder.

19. Device according to claim 1, wherein the gas generator comprises an ignition system for initiating combustion of the peripheral energetic material.

20. A needleless injection device for injecting a liquid active principle, the device comprising:
   a pyrotechnic charge formed of a central energetic material and a peripheral energetic material that surrounds the central energetic material such that an entire outer surface of the central energetic material contacts an inner surface of the peripheral energetic material, the central and peripheral energetic materials having different rates of combustion;
   a reserve chamber capable of housing the liquid active principle;
   an injection nozzle for injecting the liquid active principle; and
   at least one piston that moves the liquid active principle through the reserve chamber and into the injection nozzle based on combustion of the central and peripheral energetic materials.

* * * * *